United States Patent [19]

Guillemet et al.

[11] Patent Number: 4,842,864

[45] Date of Patent: Jun. 27, 1989

[54] SELF-ADHESIVE DEVICE FOR THE PERCUTANEOUS ADMINISTRATION OF AN ACTIVE INGREDIENT

[75] Inventors: Alain Guillemet, Dijon; Eric Teillaud, Talant; Philippe Reginault, Fontaine les Dijon, all of France

[73] Assignee: Laboratories D'Hygiene et de Dietetique, Paris, France

[21] Appl. No.: 174,414

[22] Filed: Mar. 25, 1988

[30] Foreign Application Priority Data

Mar. 25, 1987 [FR] France ............................... 87 04133

[51] Int. Cl.⁴ ............................................. A61K 9/16
[52] U.S. Cl. .................................. 424/448; 424/449; 424/486
[58] Field of Search ................ 424/448, 449, 484, 486

[56] References Cited

U.S. PATENT DOCUMENTS

| 4,615,699 | 10/1986 | Gale et al. | 424/448 |
| 4,738,848 | 4/1988 | Yoshida et al. | 424/448 |
| 4,740,374 | 4/1988 | Nakano et al. | 424/448 |
| 4,746,509 | 5/1988 | Haggiage et al. | 424/449 |
| 4,776,850 | 10/1988 | Guse et al. | 424/486 |
| 4,778,678 | 10/1988 | Guse | 424/486 |
| 4,784,856 | 11/1988 | Fukuda et al. | 424/448 |

FOREIGN PATENT DOCUMENTS 0159168 10/1985 European Pat. Off. .

OTHER PUBLICATIONS

Patents Abstract of Japan, vol. 10, No. 144, (C-349)[2201], May 27, 1986 & JP-A-61 5012, (Daiichi Seiyaku K.K.) 10-01-1986.

Primary Examiner—Thurman K. Page
Attorney, Agent, or Firm—Holman & Stern

[57] ABSTRACT

The present invention relates to a novel self-adhesive matrix for the percutaneous administration of an active ingredient. This matrix comprises a combination of the following:

(a) 40 to 60 parts by weight of an ethylene/vinyl acetate copolymer material,
(b) 40 to 60 parts by weight of a higher aliphatic monoalcohol compound,
(c) 1 to 20 parts by weight of a cellulose derivative material,
(d) 0.1 to 8 parts by weight of a polyhydric alcohol compound, and
(e) 0.01 to 10 parts by weight of an active ingredient which can be administered percutaneously, the weight ratio a+c/b+d being between 0.7 and 1.3.

12 Claims, 2 Drawing Sheets

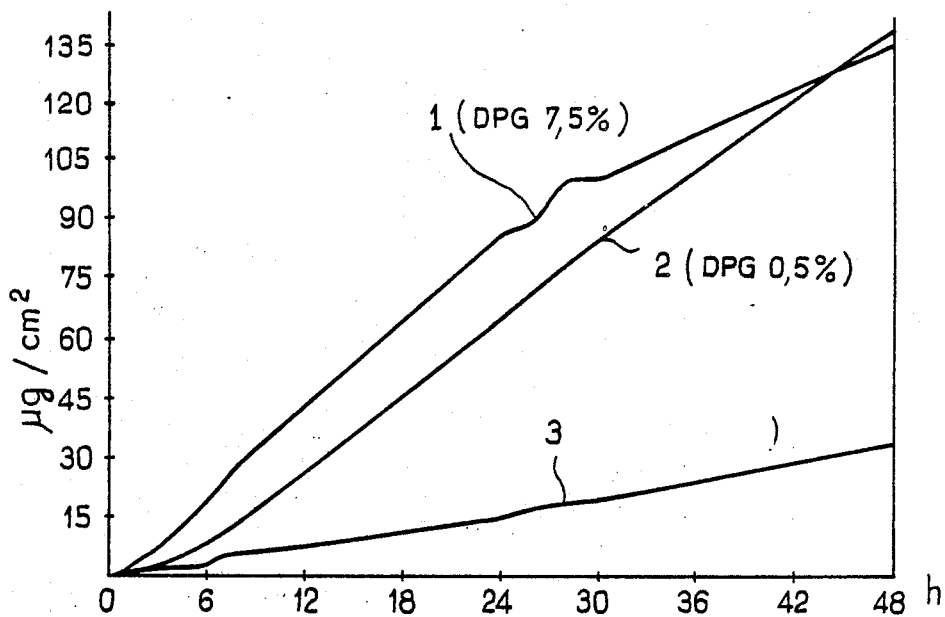
FIG_1
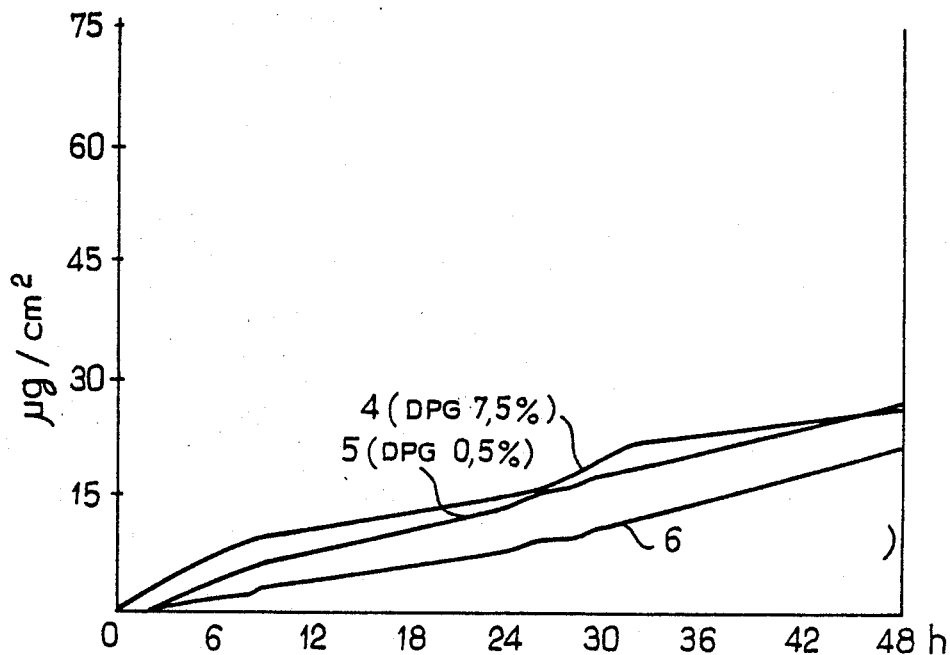
FIG_2

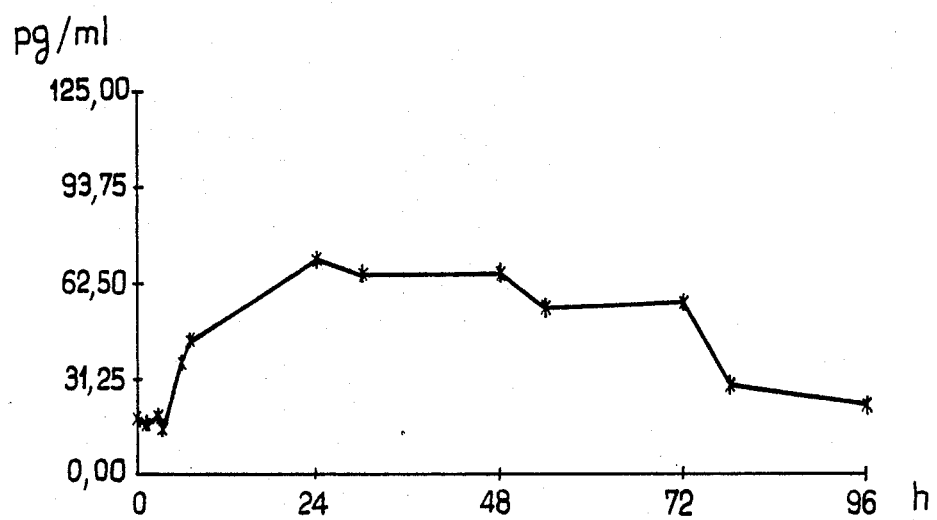
FIG_3

SELF-ADHESIVE DEVICE FOR THE PERCUTANEOUS ADMINISTRATION OF AN ACTIVE INGREDIENT

The present invention relates to a novel matrix for the percutaneous administration of an active ingredient.

The term matrix is understood here as meaning the chemical composition of ingredients enabling the percutaneous adminsitration of an active ingredient, and the term device is understood as meaning the whole consisting of the matrix and its support.

Numerous systems have already been proposed for the percutaneous administration of an active ingredient. In particular, systems for the percutaneous administration of trinitroglycerol are known for the treatment of angina pectoris. These systems, which consist of a support on which a reservoir or matrix containing the active ingredient is deposited, have the disadvantage that their adhesiveness to the skin decreases rapidly with time. In fact, in the case of a reservoir, the active ingredient is dissolved in a solvent which serves to carry the active ingredient through a microporous membrane to the skin. In the case of a matrix, the active ingredient contained in a polymer lattice is also dissolved in a solvent which serves as a carrier. As the reservoir or matrix is held on the skin by a conventional adhesive of the acrylic type, the solvent partially dissolves some of the components of the adhesive, which thus rapidly loses its effectiveness.

To overcome this disadvantage, European Patent Document No. A-0159168 has already proposed a solution whereby the matrix containing the active ingredient has properties of self-adhesion to the skin. This matrix, containing an active ingredient, consists of a water-soluble protein, a polyhydric alcohol compound, a tackifier and an oleaginous substance. More particularly, the water-soluble protein can be natural or synthetic and animal or vegetable, for example gelatin, collagen, casein or bird lime, in proportions of 5 to 50%; the polyhydric alcohol compound can be a glycol compound, for example ethylene glycol, propylene glycol, butylene glycol or polyethylene glycol, a triol compound or a polyol compound, in proportions of 5 to 50%; the tackifier can be cellulose or a derivative material, for example methyl cellulose, ethyl cellulose, propyl cellulose, methylpropyl cellulose, hyroxymethyl cellulose, hydroxyethyl cellulose, hydroxypropyl cellulose or carboxymethyl cellulose, a polysaccharide compound, polyvinyl alcohol or polyvinylpyrrolidone, in proportions of 0.1 to 15%; and the oleaginous substance can be a fatty acid ester, paraffin, lanolin, a higher aliphatic monoalcohol compound, for example octyldodecyl, palmityl, stearyl or myristyl alcohol, or silicone oil, in proportions of 0.1 to 25%.

The novel technical solution now proposed uses a self-adhesive matrix which differs from the prior art referred to above by the nature of the main constituent, by the proportions of the other constituents and also by the ease of industrial processing.

The self-adhesive matrix according to the invention for the percutaneous administration of an active ingredient comprises:

(a) 40 to 60 parts by weight of an ethylene/vinyl acetate copolymer material,
(b) 40 to 60 parts by weight of a higher aliphatic monoalcohol compound,
(c) 1 to 20 parts by weight of a cellulose derivative material,
(d) 0.1 to 8 parts by weight of a polyhydric alcohol compound, and
(e) 0.01 to 10 parts by weight of an active ingredient which can be administered percutaneously, the weight ratio a+c/b+d being between 0.7 and 1.3.

Advantageously, the ethylene/vinyl acetate (EVA) copolymer material used will have a content of vinyl acetate units of between 35 and 55% by weight, preferably of the order of 45% by weight, relative to the weight of the ethylene/vinyl acetate copolymer material.

The term higher aliphatic monoalcohol compound is understood here as meaning saturated or unsaturated monoalcohol compounds having 12 to 20 carbon atoms, for example 2-octyldodecan-1-ol, palmityl alcohol, stearyl alcohol or myristyl alchohol.

The term cellulose derivative material is understood here as meaning alkyl celluloses, for example methyl cellulose, ethyl cellulose, propyl cellulose or methylpropyl cellulose, and hydroxyalkyl celluloses, for example hydroxymethyl cellulose, hydroxyethyl cellulose or hydroxypropyl cellulose.

The term polyhydric alcohol compound is understood here as meaning glycol compounds, for example ethylene glycol, propylene glycol, butylene glycol, triethylene glycol, diethylene glycol, polyethylene glycol or polypropylene glycol.

The term active ingredient is understood here as meaning any solid or liquid product which can be absorbed through the skin and which is at least partially soluble in the phase of polyhydric alcohol compound/higher aliphatic monoalcohol compound. Preference will be given to steroids and more particularly estradiol, especially $\beta$-estradiol, estradiol derivative materials, especially the acetates, for example estradiol 17-acetate or estradiol 3,17-diacetate, progesterone and its derivative materials, testosterone and its derivative materials, and corticosteroids.

In practice, preference will be given to an active ingredient content which is such that all the said active ingredient is dissolved in the phase of polyhydric alcohol compound/higher aliphatic monoalcohol compound, and preference will be given to formulations which are such that the ratio of the solvent phase (higher aliphatic monoalcohol compound/polyhydric alcohol compound) to the polymer phase (EVA/cellulose derivative material) is about one.

BRIEF DESCRIPTION OF THE DRAWINGS

FIG. 1 and FIG. 2 show the percentage estradiol released as a function of time.

FIG. 3 shows the mean level of plasma estradiol.

In a preferred embodiment of the invention, the self-adhesive device for the percutaneous administration of an active ingredient comprises a support coated with a matrix consisting of:

(a) 40 to 60 parts by weight of an ethylene/vinyl acetate copolymer material,
(b) 40 to 60 parts by weight of 2-octyldodecan-1-ol,
(c) 1 to 20 parts by weight of ethyl cellulose,
(d) 0.1 to 8 parts by weight of dipropylene glycol, and
(e) 0.01 to 10 parts by weight of estradiol, the weight ratio a+c/b+d being between 0.7 and 1.3.

More precisely, in this preferred embodiment of the invention, it will be advantageous to use about 45 parts by weight of EVA having a content of vinyl acetate units of the order of 45%, about 40 to 45 parts by weight of 2-octyldodecan-1-ol, about 5 to 10 parts by weight of ethyl cellulose with a viscosity of between $2 \times 10^{-2}$ and $2 \times 10^{-1}$ Pa.s, about 1 to 5 parts by weight of dipropylene glycol and about 3 to 5 parts by weight of β-estradiol.

The support receiving the matrix may be any flexible support which is impermeable to the constituents of the matrix and which has a thickness of between 50 and 500 micrometers. Preference will be given to a polymer support, for example polyethylene, polypropylene, polyesters or polyethylene foams, especially microcellular cellular ones, known in particular in the field of bandages.

In practice, the matrix may be covered with a protective film which can be peeled off before the device is used, and the device itself may be packaged in a leak-tight form of protection, for example a polyethylene/aluminum composite.

The self-adhesive device according to the invention for the percutaneous administration of an active ingredient does not stick immediately on contact with the skin but has a progressive adhesive strength which increases a few minutes after it has been placed on a subject's skin. The device or matrix can easily be removed without desquamation of the skin and then put back, retaining an identical adhesive strength. This is particularly advantageous for a device of this type which the subject has to keep on for several days; he can thus remove the said device temporarily, for example when taking a bath.

The device according to the invention has the further advantage of being reduced to a minimum area and a minimum thickness. By virtue of its own adhesive strength, it is not necessary to apply an adhesive compound around the edge of the active part of the device. The whole surface of the device is both active and adhesive. Thicknesses of a few hundred micrometers of matrix (150 to 250 micrometers) will suffice to administer the necessary amount of active ingredient through the skin for several days.

According to the invention, a method for the preparation of a self-adhesive matrix for percutaneous administration is recommended which comprises the following steps;

(1) the means (a) and part of the means (b) are mixed, with stirring, at a temperautre greater than or equal to 110° C.,
(2) the means (c) is incorporated into the mixture resulting from stage 1, with stirring, at a temperature greater than or equal to 110° C., and then homogenized,
(3) the remainder of the means (b) is incorporated into the mixture resulting from stage 2, with stirring, at a temperature greater than or equal to 110° C.,
(4) the resulting mixture obtained in this way is homogenized at a temperature greater than or equal to 110° C. and then left to stand for at least 8 hours.
(5) the resulting mixture obtained in this way is heated at a temperature of 50°–70° C., preferably 60° C., for at least 0.25 h, after which the means (d) and the active ingredient in a solvent for the said active ingredient, for example ethanol, are incorporated at this temperature,
(6) the resulting mixture is homogenized for at least 0.5 h without heating,
(7) the resulting mixture homogenized in this way is deposited on a temporary support, especially silicone-treated paper, at a temperature of the order of 50°–70° C., at a rate of 100 to 300 g/m²,
(8) the whole comprising the said temporary support and the matrix is heated at a temperature of the order of 70°–90° C. in order to evaporate the solvent for the active ingredient until the residual proportion is less than 5% by weight, and
(9) the resulting dry matrix is transferred onto an appropriate support.

The industrial production of the device according to the invention is facilitated by the fact that the matrix charged with active ingredient is malleable and can also be coated onto a support by the so-called "fusion" technique, i.e. by fusion in the absence of solvent. Whichever coating technique is employed (solvent phase or "fusion" technique), it is thus possible to coat large areas and then cut the device to the desired size, which is calculated according to the amount of active ingredient present per unit area and the amount of active ingredient to be administered to the subject over a given time.

This simple manufacturing technique of cutting to a variable area is particularly advantageous for marketing devices of different sizes, capable of administering different amounts of active ingredient. It is known in fact that, for certain active ingredients, especially steroidal hormones, the individual variations in the subjects treated are very large and the dosage must be adapted to each subject.

The invention will be understood more clearly from the following description of preparative examples, permeation tests and clinical results.

PREPARATION I

Example 1

1575 g of LEVAPREN 450P$^R$ (EVA having a content of vinyl acetate units of 45%, marketed by BAYER) and 980 g of EUTANOL G$^R$ (2-octyldodecanol marketed by HENKEL) are introduced into a 5-liter malaxator. The temperature is raised to 140° C. and 350 g of ETHOCEL 20$^R$ (ethyl cellulose with a viscosity of $2 \times 10^{-2}$ Pa.s) are added to the mixture in small portions. After homogenization of the medium, 490 g of EUTANOL G$^R$ are added. The whole is homogenized for 0.5 hour and left to stand for 24 hours. The composition is then heated at 60° C. for 0.5 hour and a solution of 105 g of dipropylene glycol (DPG) and 175 g of 17-β-estradiol in 875 g of anhydrous ethanol is added. The whole is homogenized for 1 hour without heating. This composition is coated onto a 105 mm wide piece of silicone-treated paper at a temperature of 60° C., at a rate of 190±5 g/m². After the coated silicone-treated paper has been heated to 80° C. in order to evaporate the ethanol to a proportion of less than 3.5% by weight, the matrix is transferred onto a polyethylene support. 20 cm² rectangular shapes with rounded corners are then cut out and packaged in heat-sealed aluminum/polyethylene sachets.

PREPARATION II

Example 2

1575 g of LEVAPREN 450P$^R$, 1050 g of EUTANOL G$^R$ and 175 g of ETHOCEL 20$^R$ are mixed at 140° C., analogously to preparation I, and 525 g of EUTANOL G$^R$ are then added. 175 g of dipropylene glycol and 175 g of 17-β-estradiol in 875 g of anhydrous ethanol are then added at 60° C. The subsequent procedure is identical to that of preparation I.

PREPARATION III

Example 3

1575 g of LEVAPREN 450P$^R$, 990 g of EUTANOL G$^R$ and 175 g of ETHOCEL 20$^R$ are mixed at 140° C., analogously to preparation I, and 497.5 g of EUTANOL G$^R$ are then added. 262.5 g of dipropylene glycol and 175 g 17-β-estradiol in 875 g of anhydrous ethanol are then added at 60° C. The subsequent procedure is identical to that of preparation I, a piece of silicone-treated paper being coated at a rate of 200±5 g/m$^2$ so as to leave a residual proportion of ethanol of less than 1.5% by weight.

PREPARATION IV

Example 4

1610 g of LEVAPREN 450P$^R$, 1070 g of EUTANOL G$^R$ and 262.5 g of ETHOCEL 20$^R$ are mixed at 140° C., analogously to preparation I, and 540 g of EUTANOL G$^R$ are then added. 175. g of dipropylene glycol and 175 g of 17-β-estradiol in 875 g of anhydrous ethanol are then added at 60° C. The subsequent procedure is identical to that of preparation I, a piece of silicone-treated paper being coated at a rate of 200±5 g/m$^2$ so as to leave a residual proportion of ethanol of less than 1.5% by weight.

PREPARATION V

Example 5

Preparation of a coating by the so-called "fusion" technique 5639 g of LEVAPREN 450P$^R$ are mixed with 4330 g of EUTANOL G$^R$ and 1031 g of ETHOCEL 20$^R$ in a 17 l malaxator by a procedure analogous to that described in preparation I. The mixture is then heated at 130° C. for 90 minutes, with moderate stirring. The composition obtained is cooled, left to stand at room temperature for 24 h and then heated to 60° C. in a malaxator. After the composition has softened, a suspension consisting of 546 g of 17-β-estradiol in 283 g of dipropylene glycol is introduced. Malaxation is continued at 60° C. for a further 1 hour. The polymer composition obtained in this way is introduced into a coating apparatus of the hot-melt type and heated at 100° C. This composition is then coated onto a 35 μm thick, 100 mm wide silicone-treated polyester support at a temperature of 105° C. and at a rate of 150±5 g/m$^2$. Transfer onto a polyethylene support is effected immediately after coating. The composite obtained is stabilized by heating in an oven to 60°±5° C.

Permeation kinetics were carried out on hairless mouse skin in a static cell of the "Franz" type, elution being carried out with a physiological serum/ethanol/PEG 400 mixture (60/20/20, v/v/v) at 37° C., and a comparison was made with the product sold by CIBA GEIGY under the trademark ESTRADERM$^R$ (curve 3). The mean results obtained from 15 samples prepared according to preparations III and IV are brought together in FIG. 1, which shows the percentage of estradiol released in μg/cm$^2$ as a function of time in hours (curve 1 with 7.5% of DPG and curve 2 with 0.5% of DPG).

Permeation kinetics on human stratum corneum were also carried out in an identical manner by comparison with ESTRADERM$^R$ (curve 6). FIG. 2 shows the mean results obtained from 15 samples prepared according to preparations III and IV (curve 4 with 7.5% of DPG and curve V with 0.5% of DPG).

It is apparent from these results that the flow of estradiol obtained with the devices according to the invention is significantly greater than that obtained with ESTRADERM$^R$ on mouse skin and comparable to that obtained with ESTRADERM$^R$ on human stratum corneum.

FIG. 3 shows the mean level of plasma estradiol obtained in 6 menopausal women who had worn a 20 cm$^2$ device prepared according to preparation I for three days. It is observed that the mean kinetics obtained are comparable to those obtained with the device marketed by CIBA GEIGY under the trademark ESTRADERM$^R$, described in FIG. 5, page 95, in Journal of Controlled Release, 2 (1985) 89–97. It appears, however, that the device according to the invention does not cause a plasma peak at the start of the treatment. No allergic manifestations were noted during this study.

What is claimed is:

1. A self-adhesive matrix for the percutaneous administration of an active ingredient, which comprises:
   (a) 40 to 60 parts by weight of an ethylene/vinyl acetate copolymer material,
   (b) 40 to 60 parts by weight of a higher aliphatic monoalcohol compound,
   (c) 1 to 20 parts by weight of a cellulose derivative material,
   (d) 0.1 to 8 parts by weight of a polyhydric alcohol compound, and
   (e) 0.01 to 10 parts by weight of an active ingredient which can be administered percutaneously,
   the weight ratio a+c/b+d being between 0.7 and 1.3.

2. A self-adhesive matrix for the percutaneous administration of an active ingredient, which comprises:
   (a) 40 to 60 parts by weight of an ethylene/vinyl acetate copolymer material,
   (b) 40 to 60 parts by weight of a higher aliphatic monoalcohol compound,
   (c) 1 to 20 parts by weight of a cellulose derivative material,
   (d) 0.1 to 8 parts by weight of a polyhydric alcohol compound, and
   (e) 0.01 to 10 parts by weight of a steroid selected from the group consisting of estradiol, progesterone, testosterone and derivative materials thereof, and corticosteroids,
   the weight ratio a+c/b+d being between 0.7 and 1.3.

3. The matrix as claimed in claim 1, wherein the ethylene/vinyl acetate copolymer material has a content of vinyl acetate units of between 35 and 55% by weight, relative to the weight of the said copolymer material.

4. The matrix as claimed in claim 3, wherein the ethylene/vinyl acetate copolymer material has a content of vinyl acetate units of the order of 45% by weight, relative to the weight of the said copolymer material.

5. The matrix as claimed in claim 1, wherein the higher aliphatic monoalcohol compound is selected from the group consisting of saturated or unsaturated monoalcohol compounds having from 12 to 20 carbon atoms.

6. The matrix as claimed in claim 1, wherein the cellulose derivative material is selected from the group consisting of alkyl celluloses and hydroxyalkyl celluloses.

7. The matrix as claimed in claim 1, wherein the cellulose derivative material is selected from the group consisting of methyl cellulose, ethyl cellulose, propyl cellulose, methylpropyl cellulose, hydroxymethyl cellulose, hydroxyethyl cellulose and hydroxypropyl cellulose.

8. The matrix as claimed in claim 1, wherein the polyhydric alcohol compound is a glycol compound selected from the group consisting of alkylene glycols.

9. The matrix as claimed in claim 8, wherein the glycol compound is selected from the group consisting of ethylene glycol, propylene glycol, butylene glycol, triethylene glycol, diethylene glycol, polyethylene glycol and polypropylene glycol.

10. The matrix as claimed in claim 1, which comprises:
   (a) 40 to 60 parts by weight of an ethylene/vinyl acetate copolymer material,
   (b) 40 to 60 parts by weight of 2-octyldodecan-1-ol,
   (c) 1 to 20 parts by weight of ethyl cellulose,
   (d) 0.1 to 8 parts by weight of dipropylene glycol, and
   (e) 0.01 to 10 parts by weight of estradiol,
the weight ratio a+c/b+d being between 0.7 and 1.3.

11. The matrix as claimed in claim 1 which comprises:
   (a) about 45 parts by weight of an ethylene/vinyl acetate copolymer containing about 45% by weight of vinyl acetate units, relative to the weight of the said copolymer material,
   (b) 40 to 45 parts by weight of 2-octyldodecan-1-ol,
   (c) 5 to 10 parts by weight of ethyl cellulose with a viscosity of between $2 \times 10^{-2}$ and $2 \times 10^{-1}$ Pa.s,
   (d) 1 to 5 parts by weight of dipropylene glycol, and
   (e) 3 to 5 parts by weight of $\beta$-estradiol.

12. A method for the preparatoin of a matrix as claimed in claim 1, wherein:
   (1) the means (a) and part of the means (b) are mixed, with stirring, at a temperature greater than or equal to 110° C.
   (2) the means (c) is incorporated into the mixture resulting from stage 1, with stirring, at a temperature greater than or equal to 110° C. , and then homogenized.
   (3) the remainder of the means (b) is incorporated into the mixture resulting from stage 2, with stirring, at a temperature greater than or equal to 110° C.,
   (4) the resulting mixture obtained in this way is homogenized at a temperature greater than or equal to 110° C. and then left to stand for at least 8 hours,
   (5) the resulting mixture obtained in this way is heated at a temperature of 50°-70° C., preferably 60° C. , for at least 0.25 h, after which the means (d) and the active ingredient in a solvent for the said active ingredient are then incorporated at this temperature.
   (6) the resulting mixture is homogenized for at least 0.5 h without heating,
   (7) the resulting mixture homogenized in this way is deposited on a temporary support, especially silicone-treated paper, at a temperature of the order of 50°-70° C., at a rate of 100 to 300 g/m², 
   (8) the whole comprising the said temporary support and the matrix is heated at a temperature of the order of 70°-90° C. in order to evaporate the solvent for the active ingredient until the residual proportion is less than 5% by weight, and
   (9) the resulting dry matrix is transferred onto an appropriate support.

* * * * *